US008571676B2

(12) United States Patent
Gibson

(10) Patent No.: US 8,571,676 B2
(45) Date of Patent: *Oct. 29, 2013

(54) IMPLANTABLE DEVICE HAVING OSSEOINTEGRATING PROTUBERANCES

(75) Inventor: Peter Gibson, South Coogee (AU)

(73) Assignee: Cochlear Limited, Macquarie Univeristy, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,927

(22) Filed: May 3, 2011

(65) Prior Publication Data
US 2011/0208303 A1 Aug. 25, 2011

Related U.S. Application Data

(62) Division of application No. 10/825,359, filed on Apr. 16, 2004, now Pat. No. 7,937,156.

(30) Foreign Application Priority Data

Apr. 17, 2003 (AU) ................................ 2003901867

(51) Int. Cl.
*A61N 1/08* (2006.01)
(52) U.S. Cl.
USPC ........................................................ 607/57
(58) Field of Classification Search
USPC ........... 607/50–52, 55–57, 136–137; 600/379
See application file for complete search history.

(56) References Cited

U.S. PATENT DOCUMENTS

| 2,487,038 A | 11/1949 | Baum |
| 2,641,328 A | 6/1953 | Beaudry |
| 4,055,233 A | 10/1977 | Huntress |
| 4,333,469 A | 6/1982 | Jeffcoat et al. |
| 4,488,561 A | 12/1984 | Doring |
| 4,532,930 A | 8/1985 | Crosby et al. |
| 4,612,915 A | 9/1986 | Hough et al. |
| 4,744,792 A | 5/1988 | Sander et al. |
| 4,904,233 A | 2/1990 | Hankansson et al. |
| 4,986,831 A | 1/1991 | King et al. |
| 5,176,620 A | 1/1993 | Gilman |
| 5,277,694 A | 1/1994 | Leysieffer et al. |

(Continued)

FOREIGN PATENT DOCUMENTS

| RU | 2282426 | 8/2008 |
| WO | WO-8300999 | 3/1983 |

(Continued)

OTHER PUBLICATIONS

Gibson, "Mechanical Design for a Cochlear Implant", assigned U.S. Appl. No. 10/523,795, filed Feb. 9, 2005, 30 pages.

(Continued)

*Primary Examiner* — Rex R Holmes
(74) *Attorney, Agent, or Firm* — Kilpatrick, Townsend & Stockton LLP.

(57) ABSTRACT

A housing for an implantable device for mounting to a patient's bone is disclosed. The housing comprises one or more surfaces, wherein at least one of the surfaces is substantially orthogonal to an implant axis and is configured to abut the patient's bone, and a first osseointegrating protuberance extending from one of the surfaces, wherein a longitudinal axis of the first protuberance is disposed at an acute first angle relative to the implant axis.

21 Claims, 7 Drawing Sheets

(56) References Cited

U.S. PATENT DOCUMENTS

| | | | |
|---|---|---|---|
| 5,282,253 | A | 1/1994 | Konomi |
| 5,443,493 | A | 8/1995 | Byers et al. |
| 5,558,618 | A | 9/1996 | Maniglia |
| 5,572,594 | A | 11/1996 | Devoe et al. |
| 5,738,521 | A | 4/1998 | Dugot |
| 5,814,095 | A | 9/1998 | Muller et al. |
| 5,881,158 | A | 3/1999 | Lesinski et al. |
| 5,906,635 | A | 5/1999 | Maniglia |
| 5,999,632 | A | 12/1999 | Leysieffer et al. |
| 6,042,380 | A | 3/2000 | De Rowe |
| 6,070,105 | A | 5/2000 | Kuzma |
| 6,125,302 | A | 9/2000 | Kuzma |
| 6,132,384 | A | 10/2000 | Christopherson et al. |
| 6,381,336 | B1 | 4/2002 | Lesinski et al. |
| 6,427,086 | B1 | 7/2002 | Fischell et al. |
| 6,516,228 | B1 | 2/2003 | Berrang et al. |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,697,674 | B2 | 2/2004 | Leysieffer |
| 6,730,015 | B2 | 5/2004 | Schugt et al. |
| 6,840,919 | B1 * | 1/2005 | Håkansson .......... 604/175 |
| 7,043,040 | B2 | 5/2006 | Westerkull |
| 7,937,156 | B2 * | 5/2011 | Gibson .......... 607/57 |
| 2002/0019669 | A1 * | 2/2002 | Berrang et al. .......... 623/10 |
| 2003/0135216 | A1 * | 7/2003 | Sevrain .......... 606/73 |
| 2004/0260361 | A1 | 12/2004 | Gibson |
| 2006/0030852 | A1 * | 2/2006 | Sevrain .......... 606/73 |
| 2006/0116743 | A1 | 6/2006 | Gibson et al. |
| 2009/0099658 | A1 | 4/2009 | Dalton et al. |

FOREIGN PATENT DOCUMENTS

| | | |
|---|---|---|
| WO | WO-9429932 | 12/1994 |
| WO | WO-9705673 | 2/1997 |
| WO | WO-9736457 | 10/1997 |
| WO | WO-9906108 | 2/1999 |
| WO | WO-0071063 | 11/2000 |
| WO | WO-0110369 | 2/2001 |
| WO | WO-03070133 | 8/2003 |
| WO | WO-03092326 | 11/2003 |
| WO | WO-2004014269 | 2/2004 |
| WO | WO-2004014270 | 2/2004 |
| WO | WO-2007053882 | 5/2007 |

OTHER PUBLICATIONS

Niznick, "Achieving Osseointegration in Soft Bone: The Search for Improved Results," Oral Health, Aug. 2000, pp. 27-32.

International Preliminary Examination Report, issued in connection with International Patent Application No. PCT/AU03/01004, dated Nov. 22, 2004.

International Search Report, issued in connection with International Patent Application No. PCT/AU03/01004, dated Oct. 13, 2003.

Written Opinion, issued in connection with International Patent Application No. PCT/AU03/01004, dated Jan. 9, 2006.

International Preliminary Report on Patentability, issued in connection with International Patent Application No. PCT/AU06/001632, dated May 14, 2008.

International Search Report, issued in connection with International Patent Application No. PCT/AU06/001632, dated Dec. 1, 2006.

Written Opinion, issued in connection with International Patent Application No. PCT/AU06/001632, dated Dec. 1, 2006.

International Preliminary Examination Report, issued in connection with International Patent Application No. PCT/AU2000/000936, dated Jun. 8, 2001.

International Search Report, issued in connection with International Patent Application No. PCT/AU2000/000936, dated Oct. 10, 2000.

International Preliminary Examination Report, issued in connection with International Patent Application No. PCT/AU2003/000229, dated May 24, 2004.

International Search Report, issued in connection with International Patent Application No. PCT/AU2003/000229, dated May 5, 2003.

Written Opinion issued in connection with International Patent Application No. PCT/AU2003/00229, dated Jun. 30, 2003.

International Preliminary Examination Report, issued in connection with International Patent Application No. PCT/AU2003/001012, dated Nov. 23, 2004.

International Search Report, issued in connection with International Patent Application No. PCT/AU2003/001012, dated Oct. 13, 2003.

Written Opinion, issued in connection with International Patent Application No. PCT/AU2003/001012, dated Feb. 23, 2004.

* cited by examiner

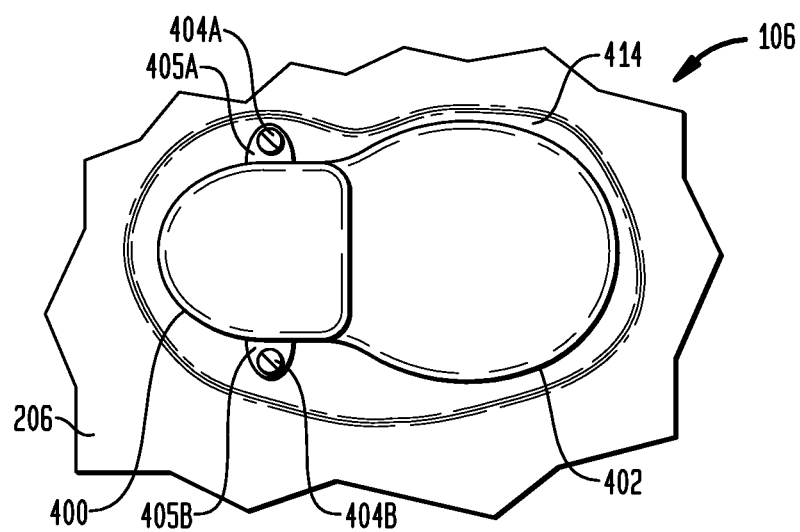
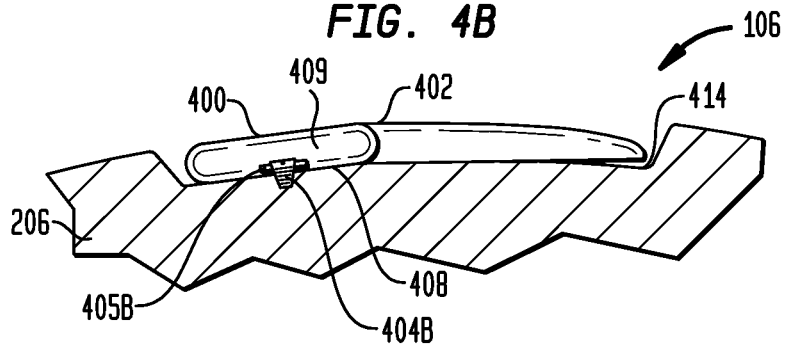

IMPLANTABLE DEVICE HAVING OSSEOINTEGRATING PROTUBERANCES

CROSS-REFERENCE TO RELATED APPLICATIONS

This application is a divisional of U.S. patent application Ser. No. 10/825,359, filed on Apr. 16, 2004, now U.S. Pat. No. 7,937,156, which claims priority from Australian Provisional Patent Application No. 2003901867, filed on Apr. 17, 2003. Each of these documents is hereby incorporated by reference herein.

BACKGROUND

1. Field of the Invention

The present invention relates generally to implantable devices and, more particularly, to implantable devices having osseointegrating protuberances.

2. Related Art

Medical devices often include one or more components that are permanently or temporarily implanted in a patient. Many such implantable devices are designed to be mounted adjacent to, abutting, or in the surface of one or more bones. Various techniques have been implemented in order to fix such devices in place and to ensure that the devices do not undergo movement once implanted.

In one conventional approach, an implantable device is the housing for a receiver/stimulator unit has been positioned on a bone within the head of the recipient by drilling a bed or well into and through the posterior section of the mastoid bone lying behind the recipient's ear. Such a bed is usually made by drilling the bone down to the lining of the brain or dura mater, so that the receiver/stimulator unit is maintained in position and does not protrude excessively past the skull surface. The tight dimensions of the bed or well relative to the size of the housing together with the eventual growth of a fibrous capsule serves to help retain the housing in its desired position. One disadvantage of this technique is the time taken in the implant surgery to create the bed. A further disadvantage is that there is some potential for the housing to shift out of the well due to an impact to the head of the recipient. Still further, this technique is not always possible depending upon the thickness of the surrounding bone and the age and anatomy of the recipient.

Another conventional technique has involved the positioning of at least one suture or Dacron tie (bioresorbable or non-bioresorbable) across the housing to hold it in place. (DACRON is a trademark of E.I. du Pont de Nemours and Company) One problem with this approach is that drilling of the holes into the surrounding bone can be a difficult and time consuming procedure, and especially for young children, much care must be taken by the surgeon to ensure that the drilling does not perforate the dura mater, as the skull thickness in such cases can be quite thin. Further to this, the suture or Dacron ties may not be sufficiently strong enough to withstand a substantial impact to a region of the head adjacent the device and as a result, such a force may dislodge the device from its desired position. In addition, it has been found that if a suture or Dacron tie is inadvertently placed across an inappropriate section of the device, such as across a strain relief of the electrode lead, the suture/tie may cause the lead/device to undergo fatigue and cause failure at this location.

SUMMARY

In one aspect of the present invention, a housing for an implantable device for mounting to a patient's bone is disclosed. The housing comprises a surface having an abutting portion configured to abut the bone when the housing is implanted in the patient, wherein the abutting portion defines a housing axis orthogonal to the surface, and a first osseointegrating protuberance extending from the surface, wherein a longitudinal axis of the first protuberance is disposed at an acute first angle relative to the housing axis.

In another aspect of the present invention, an implantable device for mounting to a patient's bone is disclosed. The device comprises a housing including a surface having an abutting portion configured to abut the bone when the housing is implanted in the patient, wherein the abutting portion defines a housing axis orthogonal to the surface, one or more components of the device mounted in the housing, and a first osseointegrating protuberance extending from the surface, wherein a longitudinal axis of the first protuberance is disposed at an acute first angle relative to the housing axis.

In a further aspect of the present invention, an implantable component of a tissue stimulating prosthesis is disclosed. The implantable component comprises a housing including a surface having an abutting portion configured to abut the bone when the housing is implanted in the patient, wherein the abutting portion defines a housing axis orthogonal to the surface, one or more components of the prosthesis mounted in the housing, and a first osseointegrating protuberance extending from the surface, wherein a longitudinal axis of the first protuberance is disposed at an acute first angle relative to the housing axis.

BRIEF DESCRIPTION OF THE DRAWINGS

FIG. 4A is a plan view of a further embodiment of an implantable device of the present invention.

FIG. 4B is a side view of the implantable device shown in FIG. 4A.

DETAILED DESCRIPTION

Embodiments of the present invention are directed to one or more osseointegrating protrusions extending from surfaces of an implantable device to secure the device to a bone. Osseointegration is a term commonly used to describe the process in which living bone forms a biological bond to an implanted element, firmly securing the implanted element to the skeletal structure. Osseointegration is thought to occur at a molecular level where the implant becomes part of the bone to which the implant has been mounted. There is a tendency for the formation of this structural connection to continue over time, further adhering the living bone to the surface of an implant.

Embodiments of the present invention are described below in connection with one type of implantable device, a cochlear prosthetic device. Cochlear prostheses use direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, the cochlear prosthetic device provides stimulation of the cochlear nucleus in the brainstem.

Exemplary cochlear prostheses in which the present invention may be implemented include, but are not limited to, those systems described in U.S. Pat. Nos. 4,532,930, 6,537,200, 6,565,503, 6,575,894 and 6,697,674. As described therein, cochlear prostheses generally include an external, wearable control unit that determines a pattern of electrical stimulation that is provided to an implanted stimulator unit containing active circuitry in a hermetic enclosure. Electrical stimulation channels are routed through electrodes to provide electrical stimulation of auditory nerve cells.

Figure 1:
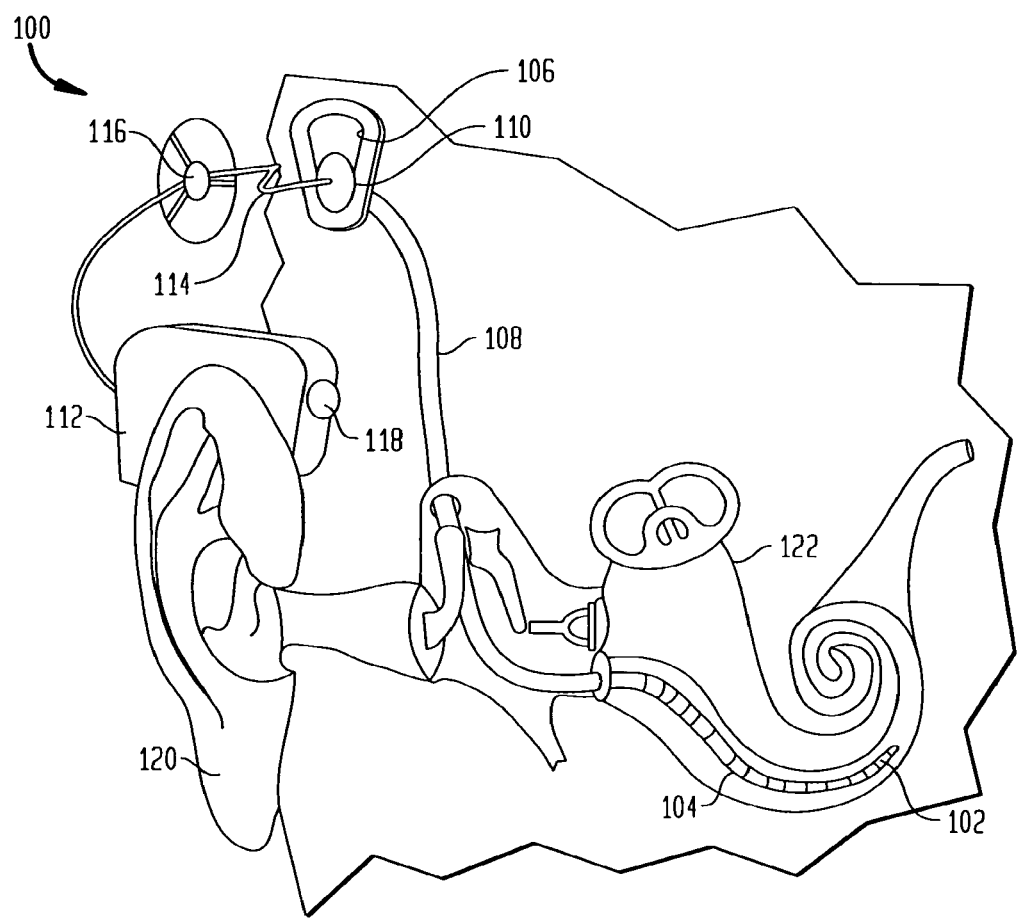
FIG. 1 is simplified diagram of a cochlear prosthetic device suitable for implementing the implantable device housing of the present invention.

FIG. 1 is a schematic diagram of an exemplary cochlear implant system or prosthetic device 100 in which embodiments of the present invention may be implemented. In the context of such an application, embodiments of the present invention are directed to a carrier member of an electrode array 104 which has a holding member disposed on the surface thereof for the surgeon to grasp during insertion or implantation of the electrode array into the cochlea 122 of a recipient (also referred to herein as a patient).

Once implanted, electrodes 102 of the electrode array 104 receive stimulation signals from a stimulator unit 106. Stimulator unit 106 is typically electrically connected to electrode array 104 by way of electrical lead 108. Lead 108 is preferably continuous with no electrical connectors external the housing of stimulator unit 106.

Stimulator unit 106 is preferably positioned within a housing that is implantable within the patient. The housing for stimulator unit 106 is typically implantable within a recess in the bone behind the ear posterior to the mastoid. When implanted, the housing preferably contains, in addition to stimulator unit 106, a receiver unit 110. Receiver unit 110 is preferably adapted to receive signals 114 from a controller 112. Controller 112 is, in use, preferably mounted external to the body behind the outer ear 120 of the patient such that signals 114 are transmitted transcutaneously through the skin of the patient.

Signals 114 travel from controller 112 to receiver unit 110 and vice versa. Receiver unit 110 includes a receiver antenna, such as an antenna coil, adapted to receive radio frequency (RF) signals from a corresponding transmitter antenna 116, such as an antenna coil, worn externally of the body. The radio frequency signals may comprise frequency modulated (FM) signals. It should be appreciated that the receiver antenna may also transmit signals, and that the transmitter antenna may receive such signals. The transmitter antenna coil is preferably held in position adjacent the implanted location of the receiver antenna coil by way of respective attractive magnets (not shown) mounted centrally in, or at some other position relative to, the coils.

External controller 112 comprises a speech processor (not shown) adapted to receive signals output by a microphone 118. During use, microphone 118 is preferably worn on the pinna of the recipient, however, other suitable locations may be envisaged, such as a lapel of the recipient's clothing. The speech processor encodes the sound detected by microphone 118 into a sequence of electrical stimuli in accordance with speech coding strategies now or later developed for cochlear implant systems. The encoded sequence is transferred to the implanted receiver/stimulator unit using the transmitter and receiver antennae. The implanted receiver/stimulator unit demodulates the signals and allocates the electrical pulses to the appropriate electrode 102 by an algorithm which is consistent with the chosen speech coding strategy.

External controller 112 may further comprise a power supply (not shown). The power supply may comprise one or more rechargeable batteries. The transmitter and receiver antennae are used to provide power via transcutaneous induction to the implanted receiver/stimulator unit and the electrode array.

While cochlear implant system 100 is described as having external components, in another embodiment, the controller, including the microphone, speech processor and power supply may also be implantable. In such embodiments, the controller may be contained within a hermetically sealed housing or the housing used for stimulator unit 106.

It should be appreciated that although embodiments of the present invention are described herein in connection with cochlear prosthetic device 100, the same or other embodiments of the present invention may be implemented in any implantable device now or later developed, including implantable devices included in other tissue-stimulating prosthetic systems. Examples of such devices include, but are not limited to, other sensory prosthetic devices, neural prosthetic devices, and functional electrical stimulation (FES) systems. In sensory prostheses, information is collected by electronic sensors and delivered directly to the nervous system by electrical stimulation of pathways in or leading to the parts of the brain that normally process a given sensory modality. Neural prostheses are clinical applications of neural control interfaces whereby information is exchanged between neural and electronic circuits. FES devices are used to directly stimulate tissue having contractile cells to produce a controlled contraction of the same.

Generally, the osseointegrating protuberance extends from the housing toward the bone when the device is in an implant orientation adjacent the bone. The longitudinal axes of the osseointegrating protuberances may lie in a same imaginary plane or be offset from each other, or may be oriented at an angle relative to an implant axis. The implant axis is substantially orthogonal with an abutting surfaces of the housing and bone, generally reflecting the direction of motion as the housing is brought into contact with the bone.

A number of features of the osseointegrating protuberances may be selected to achieve a desired implant objective. For example, apertures, ridges and the like can be included in the osseointegrating protuberance to effect a more secure retention of the protuberance. In addition to the physical features of the osseointegrating protuberances, the angle between the longitudinal axes of the osseointegrating protuberances and the implant axis can vary depending on whether a permanent or removable implantation is desired. For example, osseointegrating protuberances that are parallel with the implant axis are generally more easily extricated from the bone than those that are oriented at an angle with the implant axis. In addition, other features, such as threads, can be implemented to provide the ability to manually extricate the housing.

The osseointegrating protuberances are either formed of or coated with titanium, a titanium alloy or other material or surface treatment that encourages or facilitates osseointegration. Preferably, the remaining parts of the housing do not osseointegrate with the bone. For example, the housing may be coated with a material that prevents osseointegration, such as a biocompatible silicone, or may be formed from a biocompatible metallic, ceramic and polymeric material.

Figure 2A:
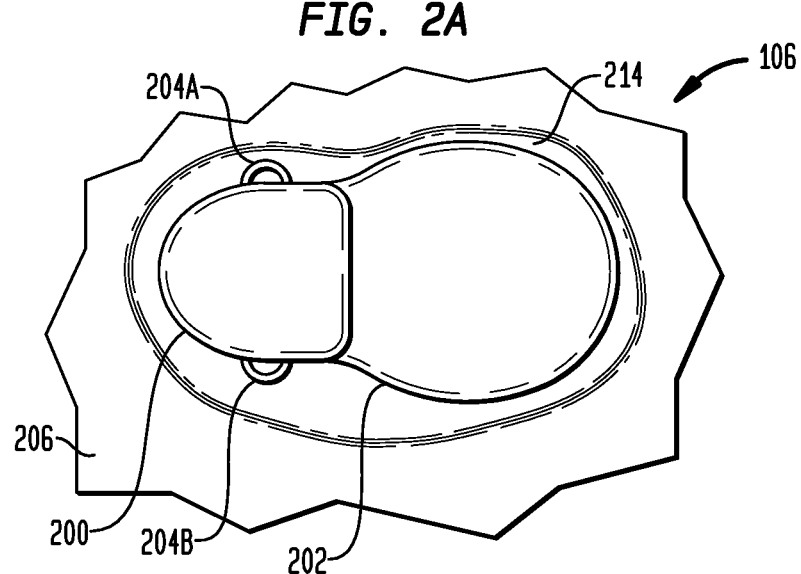
FIG. 2A is a plan view of one embodiment of an implantable device of the present invention.
Figure 2B:
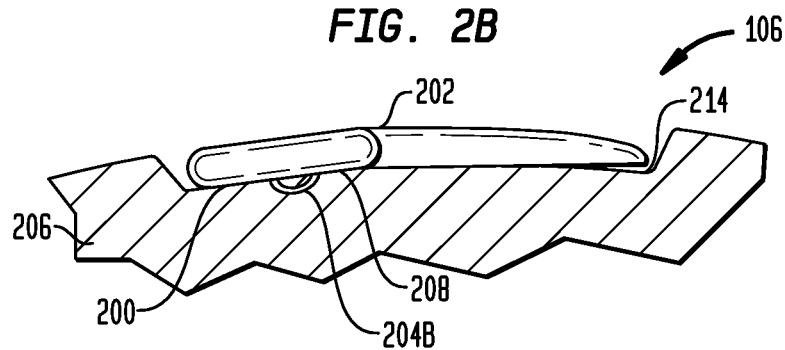
FIG. 2B is a side view of the implantable device shown in FIG. 2A.
Figure 2C:
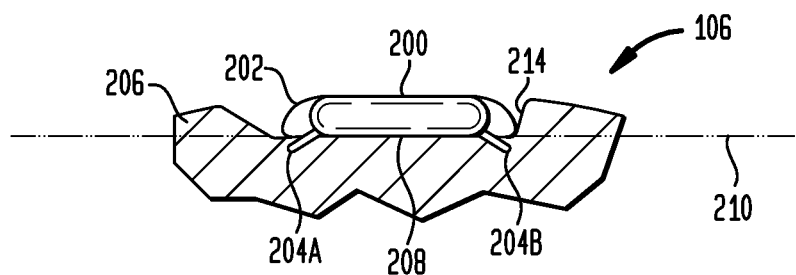
FIG. 2C is an end view of the implantable device in FIG. 2A.

FIGS. 2A-2C are plan, side and end views of one embodiment of stimulator/receiver unit 106 introduced above in connection with FIG. 1. In the embodiment shown in FIGS. 2A-2C, stimulator unit 106 has a housing 200 in accordance with one embodiment of the present invention. In this exemplary application, housing 200 is configured to have mounted therein electronics and other components (not shown) of receiver/stimulator unit 106. As such, a receiver antenna coil is operatively connected to housing 200. In this exemplary embodiment, a casing 202 is attached to housing 200. Casing 202 is preferably formed by encapsulating the receiver antenna coil in, for example, silicone.

Osseointegrating protuberances in the form of loop members 204A, 204B (collectively and generally referred to herein a loop(s) or loop member(s) 204) extend from housing 200 to engage bone 206. In this exemplary application of a stimulator/receiver unit, bone 206 is a region of a patient's skull such as posterior section of the mastoid bone.

As shown in FIGS. 2A-2C, loop members 204 extend outwardly from an abutting surface 208 of housing 202 to engage bone 206. As a result, the contour of surface 208 that abuts bone 206 generally follows the contour of the bone in the region of contact. However, given the relatively small dimensions of housing 200 and the relatively planar surface of the target region of the skull, abutting surface 208 is substantially planar and, as shown in FIG. 2D, resides in and defines a plane 210.

Figure 2D:
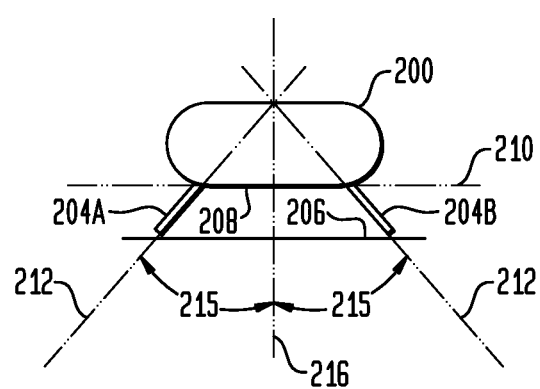
FIG. 2D is a schematic end view of the implantable device shown in FIG. 2B.

In FIG. 2D, housing 200 is shown spaced apart from the surface of bone 206, and oriented for implantation. This and similar orientations is/are referred to herein as an implant orientation. In other words, when housing 200 is oriented relative to bone 206 such that housing 200 can be brought into contact with bone 206 while maintaining such orientation to implant the device 106, housing 200 is said to be in an implant orientation.

The direction of movement to bring housing 200 into contact with bone 206 defines an implant axis 216. Given the relatively planar nature of surface 208 of housing 200, implant axis 216 is, in this exemplary application, substantially orthogonal to the imaginary plane 210 defined by surface 208.

When housing 200 is in the implant orientation adjacent to bone 206 loop members 204 extend from housing surface 208 toward bone 206. In the embodiment shown in FIG. 2D, loop members 204 extend from a surface 208 that abuts bone 206. It should be appreciated, however, that loop members 204 can extend from or be coupled to other surfaces of housing 200. As shown in FIG. 2D, loop members 204 generally have a longitudinal axis 212. Loop members 204 extend from housing surface 208 at an angle 215 relative to an implant axis 216. Angles 215 as well as the size and shape of loop members 204 are selected to enable loop members 204 to extend into bone 206 and to facilitate the osseointegration of the loop members in bone 206. The material that forms or coats protuberances 204 can be also be selected to achieve a desired degree of osseointegration. In the embodiment shown in FIG. 2D, angles 215 are approximately 45 degrees. It should be understood, however, that loop members 204 can be at any angle 215 that provides the desired degree of stability of the implanted device subsequent to sufficient osseointegration. For example, it may be desirable to insure stimulation unit 106 cannot be removed from bone 206. By orienting loop members 204 at an angle, bone formation over the loop members provides such a permanent retention in addition to the osseointegration of loop members 204. In such embodiments, then, angles 215 can range, for example, from 5 to 85 degrees. It should be appreciated, however, than angles 215 need not be within this range, as will be shown by the embodiments described below. In some such embodiments, loop members 204 may not be permanently implanted in bone 206; that is the implanted device can be extricated from bone 206.

It should also be appreciated that loop members 204 may or may not reside in the same plane. In the embodiment shown in FIGS. 2A-2D, loop members 204 reside in the same plane and, as noted, are oriented at opposing angles 215 relative to implant axis 216. In addition to insuring a more permanent implantation, such an arrangement also insures that housing 200 will experience minimal relative lateral shifting relative to bone 206.

In FIGS. 2A-2C, and the surface of the patient's skull 206 on placement of housing 200 in a periosteal pocket 214 formed in bone 206. Subsequent to implantation, loops 204 gradually sink into and osseointegrate with bone 206. In some circumstances, the time duration for substantial osseointegration is approximately 40 days. In other circumstances, the time for osseointegration to occur is more or less than 40 days. During osseointegration, housing 200 is drawn toward bone 206. Once abutting surface 208 of housing 200 comes into contact with the surface of skull 206, the implantable component 200 ceases to sink into skull 206 and is so held in place by loops 204 that have osseointegrated with the bony surface of the skull.

In accordance with the teachings of the present invention, loop members 204 are either made of, or coated with, a material that stimulates the osseointegration process. In one embodiment, loop members 204 are made of or coated with titanium or a titanium alloy. It should be appreciated, however, that loop members 204 can be made of or coated with other materials now or later developed that stimulate osseointegration.

Figure 3A:
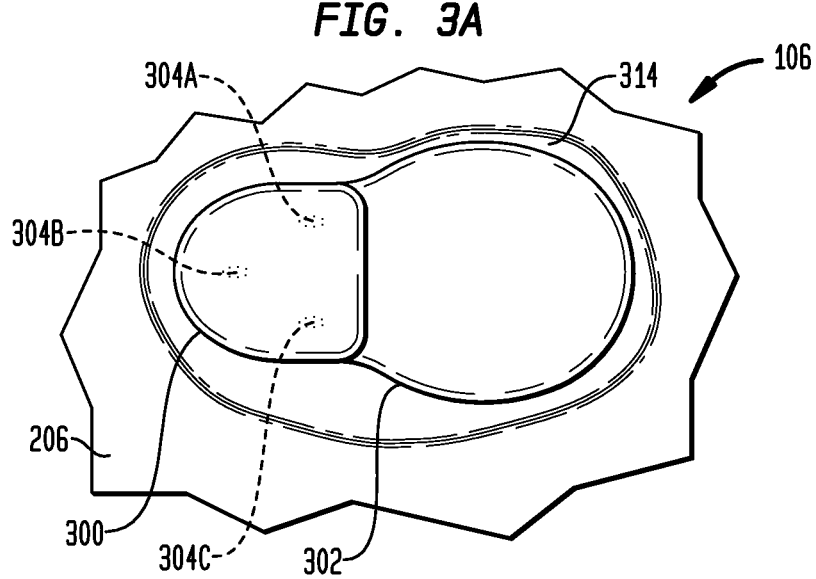
FIG. 3A is a plan view of another embodiment of an implantable device of the present invention.
Figure 3B:
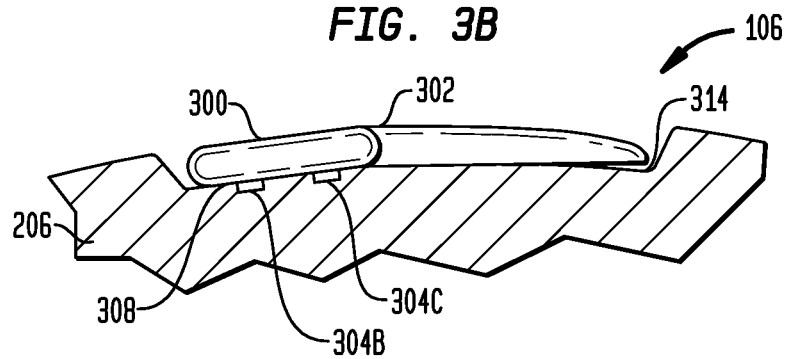
FIG. 3B is a side view of the implantable device shown in FIG. 3A.
Figure 3C:
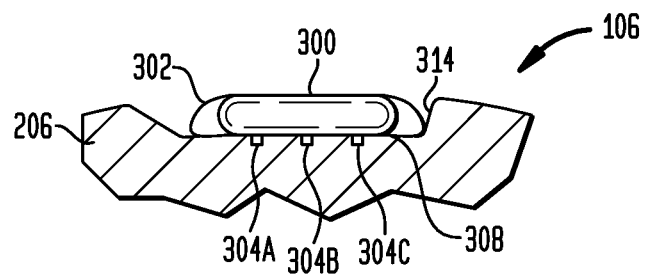
FIG. 3C is an end view of the implantable device shown in FIG. 3A.
Figure 3D:
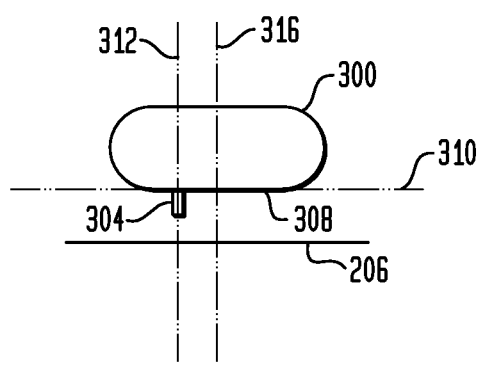
FIG. 3D is a schematic end view of the implantable device shown in FIG. 3B.

FIGS. 3A-3C are plan, side and end views of another embodiment of an implantable osseointegrating housing 300. FIG. 3D is a schematic end view of housing 300. In this embodiment, housing 300 has a casing 302 containing a receiver antenna similar to the embodiment of stimulator/receiver 106 described above in connection with FIGS. 2A-2D. Housing 300 and casing 302 are implanted in a periosteal pocket 314 in bone 206.

In this embodiment, housing 300 has three (3) studs 304A-304C (collectively and generally referred to herein as stud or studs 304) extending from an abutting surface 308 of the housing. Studs 304 are either made of, or coated with, a material that stimulates the osseointegration process. In one embodiment, studs 304 are made of or coated with titanium or a titanium alloy. It should be appreciated, however, that studs 304 can be made of or coated with other materials now or later developed that stimulate osseointegration.

Referring to FIG. 3D, abutting surface 308 of housing 300 generally defines a plane 310. Each stud 304 has a longitudinal axis 312 which is substantially parallel with implant axis 316. Studs 304 osseointegrate with the bony surface of skull 206 over time. However, due to the orthogonal orientation of studs 304 and bone 206, the orientation of studs 304 does not prevent housing 300 from being lifted away from the bony surface of skull 206 in a direction parallel with implant axis 312. To extricate studs 304, the bonds formed during osseointegration must be severed. Thus, it is preferential that studs 304 do not include additional integrating features such as apertures. It should be appreciated, however, that studs 304 serve to prevent at least substantial lateral movement of housing 300 relative to bone 306. This and similar embodiments of osseointegrating protuberances 304 may be utilized in those applications in which it may be necessary to replace the device, access housing 300 or otherwise manipulate, maintain, repair or replace an implantable component.

Figure 4C:
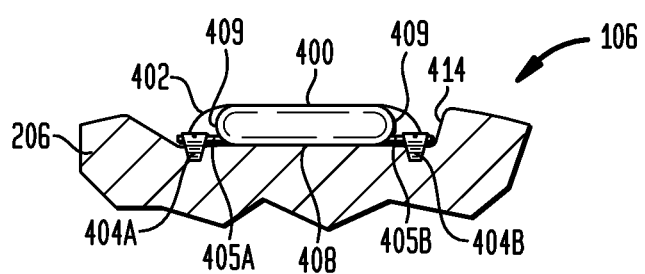
FIG. 4C is an end view of the implantable device shown in FIG. 4A.

FIGS. 4A-4C are plan, side and end views of another embodiment of an implantable osseointegrating housing 400. In this embodiment, housing 400 has a casing 402 containing a receiver antenna similar to the embodiments of stimulator/receiver 106 described above in connection with FIGS. 2A-3D. Housing 400 and casing 402 are implanted in a periosteal pocket 414 in bone 206, although, as in all embodiments, housing 400 can be implanted in other beds or wells, or simply on the surface of bone 206.

In this embodiment, housing 400 has two (2) osseointegrating protrusions in the form of threaded shafts 404A-404B (collectively and generally referred to herein as screw or screws 404) extending from a surface 409 adjacent to abutting surface 408 of the housing 400. In this exemplary embodiment, shafts 404 are threadedly mounted to respective flanges 405A, 405B. Flanges 405 extend outwardly from sidewall surfaces 409 of housing 400. It should also be appreciated that other arrangements are possible where flanges 405 extend from a different location on housing 400.

In the embodiment shown in FIGS. 4A-4C, each threaded shaft 404 is a screw having a slot in the head thereof to receive a tool, such as a screwdriver. On implantation, such screws 404 are preferably not inserted or screwed into the bony surface of bone 206. Rather, the distal end of each screw is positioned so as to abut the bony surface under pressure applied by the placement of housing 400 in periosteal pocket 414 adjacent the bony surface. Over time, screws 404 will osseointegrate with the bony surface. Should it becomes necessary to remove housing 400, screws 404 can be unscrewed from bone 206 using a screwdriver and the housing can then be lifted away from the bony surface. The screws 404 may be surgical screws and preferably have a low profile so they do not cause tissue erosion.

Threaded shafts 404 are either made of, or coated with, a material that stimulates the osseointegration process. In one embodiment, threaded shafts 304 are made of or coated with titanium or a titanium alloy. It should be appreciated, however, that threaded shafts 404 can be made of or coated with other materials now or later developed that stimulate osseointegration. Also, flanges 405 may be formed from titanium or a titanium alloy, and may be attached to a titanium housing 400 by, for example, welding. Alternatively, flanges 405 may be integrally formed with housing 400. It should also be appreciated that the flanges 405 may be made from a plastic or elastomeric materials bonded to the implant housing 400. For example, it may be possible to extend a silicone rubber coating of the implant housing 400 to create a silicone rubber flange which secured to bone 206 via screws 404. Further, it may be possible to embed a plastic material such as PTFE or polyurethane within the silicone rubber coating of implant housing 400 to form a flange, or even attach such a device to the housing via a mechanical interlock. It may also be possible to make flange 405 of a composite or combination of materials. For example, a Dacron mesh may be used as a reinforcing structure to strengthen the silicone rubber coating. PTFE, polyurethane or carbon fibre materials may also be used as a reinforcing member to form flanges 405.

By providing a flange 405 made from a plastic or elastomeric material it may be possible to allow the surgeon to remove or cut-off the flange during the surgical procedure should they not wish to use such a fixation method, resulting in the fixation mechanism of the present invention being an optional feature. Such a flange would also be easier to form and alter the shape thereof to more appropriately conform to the shape of certain bones, such as a recipient's skull. Further, a flange made from a plastic or elastomeric material is softer than a metallic flange and will therefore be less prone to causing tissue erosion. Still further, the depicted flanges could be removably mounted to the housing so allowing them to be removed if not required.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A housing for an implantable device to be secured for mounting to a patient's bone, comprising:
a surface having an abutting portion configured to abut the bone when the housing is implanted in the patient, wherein the abutting portion defines a housing axis orthogonal to the surface;
first and second osseointegrating protuberances extending from the surface, each being adapted to abut the patient's bone, wherein the first and second protuberances are divergent.

2. The housing of claim 1, wherein each of the first and second osseointegrating protuberances extends from the surface toward the bone when the abutting portion abuts.

3. The housing of claim 1, wherein the first and second osseointegrating protuberances are configured to prevent substantial relative lateral movement between the housing and the patient's bone.

4. The housing of claim 1, wherein the surface is coated with a material configured to prevent osseointegration.

5. The housing of claim 4, wherein the surface is formed of titanium coated with a biocompatible silicone.

6. The housing of claim 4, wherein the surface is formed from at least one of a biocompatible metallic, ceramic and polymeric material.

7. An implantable device for mounting to a patient's bone comprising:
a housing including a surface having an abutting portion configured to abut the bone when the housing is implanted in the patient, wherein the abutting portion defines a housing axis orthogonal to the surface;
one or more components of the device mounted in the housing; and
first and second osseointegrating protuberances extending from the surface, wherein the first and second protuberances are divergent.

8. The device of claim 7, wherein each of the first and second osseointegrating protuberances is formed of one of either titanium or a titanium alloy.

9. The device of claim 7, wherein each of the first and second osseointegrating protuberances is coated with one of either titanium or titanium alloy.

10. The device of claim 7, wherein each of the first and second osseointegrating protuberances has a surface treatment that encourages osseointegration.

11. An implantable component of a tissue stimulating prosthesis comprising:
a housing including a surface having an abutting portion configured to abut the bone when the housing is implanted in the patient, wherein the abutting portion defines a housing axis orthogonal to the surface; and
one or more components of the prosthesis mounted in the housing; and
first and second osseointegrating protuberances extending from the surface, wherein the first and second protuberances are divergent.

12. The implantable component of claim 11, wherein each of the first and second osseointegrating protuberances comprises at least one substantially smooth shaft.

13. The implantable component of claim 11, wherein each of the first and second osseointegrating protuberances comprises at least one threaded shaft.

14. The implantable component of claim 11, wherein the tissue-stimulating prosthesis is a cochlear implant.

15. The implantable component of claim 14, wherein the one or more components mounted in the housing are configured to function as a stimulator unit of the cochlear implant.

16. The housing of claim 1, wherein the angle of divergence is about a 10-170 degree angle.

17. The device of claim 7, wherein the angle of divergence is about a 10-170 degree angle.

18. The implantable component of claim 11, wherein the angle of divergence is about a 10-170 degree angle.

19. The housing of claim 1, wherein at least one of the first and second protuberances is an arcuate segment connected at both ends to the surface.

20. The device of claim 7, wherein at least one of the first and second protuberances is an arcuate segment connected at both ends to the surface.

21. The implantable component of claim 11, wherein at least one of the first and second protuberances is an arcuate segment connected at both ends to the surface.

* * * * *